United States Patent
Bellucci et al.

(10) Patent No.: US 6,923,796 B2
(45) Date of Patent: Aug. 2, 2005

(54) DIMENSIONALLY OPTIMIZED MENSTRUAL FLUID MANAGEMENT DEVICE

(75) Inventors: Remo Bellucci, S. Teresa di Spoltore (IT); Giovanni Carlucci, Chieti (IT); Rosa Cavuto, Chieti (IT); Carlo Toro, Cepagatti (IT)

(73) Assignee: The Procter & Gamble Company, Cincinnati, OH (US)

( * ) Notice: Subject to any disclaimer, the term of this patent is extended or adjusted under 35 U.S.C. 154(b) by 232 days.

(21) Appl. No.: 10/374,597

(22) Filed: Feb. 25, 2003

(65) Prior Publication Data

US 2004/0167488 A1 Aug. 26, 2004

(51) Int. Cl.[7] .......................... A61F 13/15; A61F 5/44; B65D 81/00
(52) U.S. Cl. .................. 604/385.19; 604/329; 600/574
(58) Field of Search .................... 604/327, 332, 604/333, 336, 346, 347, 355, 359, 385.01, 385.03, 385.19; 600/574

(56) References Cited

U.S. PATENT DOCUMENTS

| | | | |
|---|---|---|---|
| 3,292,626 A | | 12/1966 | Schneider |
| 3,366,116 A | | 1/1968 | Huck |
| 4,387,726 A | * | 6/1983 | Denard ....................... 600/573 |
| 4,820,291 A | * | 4/1989 | Terauchi et al. ............. 604/349 |
| 5,084,037 A | * | 1/1992 | Barnett ....................... 604/349 |
| 5,714,225 A | * | 2/1998 | Hansen et al. .............. 428/114 |
| 6,133,501 A | * | 10/2000 | Hallock et al. ............. 604/369 |
| 6,151,721 A | * | 11/2000 | Whitfield ..................... 4/144.1 |
| 6,168,584 B1 | * | 1/2001 | Allen et al. ............ 604/385.19 |
| 6,336,920 B1 | * | 1/2002 | Temple ....................... 604/355 |
| 6,685,685 B2 | * | 2/2004 | Sugita et al. ............... 604/355 |
| 6,685,687 B2 | * | 2/2004 | Mishima et al. ....... 604/385.19 |
| 6,716,204 B1 | * | 4/2004 | D'Acchioli et al. ... 604/385.19 |
| 6,761,710 B2 | * | 7/2004 | D'Acchioli et al. ... 604/385.19 |

FOREIGN PATENT DOCUMENTS

| | | |
|---|---|---|
| EP | 0 659 390 A2 | 6/1995 |
| EP | 1 104 666 A1 | 6/2001 |

* cited by examiner

Primary Examiner—Larry I. Schwartz
Assistant Examiner—Michael G. Bogart
(74) Attorney, Agent, or Firm—Kevin C. Johnson; Michael S. Kolodesh

(57) ABSTRACT

The present invention relates to a menstrual fluid management device that is attached directly to the wearer by use of an adhesive. The device allows for direct and immediate containment of menstrual and other vaginal discharges. In particular, the device improves the prevention of soiling over devices already known in the art by using an attachment flange around an orifice which has a shape of the generally oblong dimensions, where the width in the rear end of the orifice is wider than at the front end, thereby improving the circumscription of the female genitalia and the sealing along the flange to the skin of the wearer.

10 Claims, 4 Drawing Sheets

DIMENSIONALLY OPTIMIZED MENSTRUAL FLUID MANAGEMENT DEVICE

FIELD OF THE INVENTION

The present invention relates to a menstrual fluid management device that is attached directly to the wearer by use of an adhesive. The device allows for direct and immediate containment of menstrual and other vaginal discharges and thereby prevents soiling of garments whilst being comfortable to wearer, small in size and discrete. In particular, the device improves the prevention of soiling over devices already known in the art by using an attachment flange around an orifice which has a shape of generally oblong dimensions, where the width in the rear end of the orifice is wider than at the front end, thereby improving the circumscription of the female genitalia and the sealing along the flange to the skin of the wearer.

BACKGROUND TO THE INVENTION

Disposable sanitary napkin and pantiliners are well known articles of manufacture, which are designed to be placed in the genital region of the wearer to protect undergarments from soiling by absorbing the discharged fluids. As such these articles typically are formed from a liquid permeable topsheet, a liquid impermeable backsheet and an absorbent core sandwiched in-between and are attached to the undergarment of the wearer.

However these products do not provide an entirely satisfactory performance. In particular the key performance requirements of complete absorption of fluid without soiling, comfortable to wear product under all items of clothing and a small and discrete product are not fulfilled by conventional articles available despite continued development effort in the area. One key limiting factor in improvements of conventional articles is due to the fact that they are worn in an undergarment, i.e. decoupled from the body. Typically improvement in one performance attribute ultimately results in a reduced performance in another.

In order to address the absorption and comfort issues, the prior art describes the use of so called body adhesives to attach the articles directly to the skin of the wearer. In this manner the articles can be more effectively positioned so as to ensure direct absorption of the discharged fluids whilst being independent of the location of the undergarments. In this manner for example the problem of bunching which result in wearer discomfort can be reduced.

For example GB 2 284 767 discloses sanitary napkins provided with a body adhesive to attach the article the wearers' torso. U.S. Pat. No. 4,460,363 discloses pressure sensitive hot melt adhesives for sanitary products. WO 96/13228 discloses absorbent articles having an adhesive applied to the body facing surface for securement of the article to the wearer without pain upon removal.

Similarly WO 98/27918, WO 98/28023 and WO 98/81014 disclose adhesives defined in terms of rheology for secure attachment of absorbent articles to the skin which providing comfortable removal with a low and acceptable level of pain.

However the application of adhesive on the topsheet of such articles reduces the surface area of the topsheet available to absorb the discharged fluids and thus can lead to undergarment soiling. As an alternative in the art, a development has taken place in which a container having an attachment flange for secure attachment with the body adhesives described above have been developed. Such articles, as found for example in UK patent 1,092,274, were originally designed as medical devices for the collection of urine or other discharges.

A further step for the menstrual usage of a collection bag was disclosed in EP 1,104,666 and EP 0966936 in which the use of an oval flange in conjunction with a container is disclosed. EP 1,104,666 already shows that the oval/oblong of the flange/opening can be asymmetric in that the aperture and thereby also the flange on one end of the article is wider and on the other end is narrower. The reason for this design can be found in paragraph 34 in conjunction with FIG. 1 of this document from where it becomes clear that the dimension of the flange at the rearward end of the article should be narrow "such that only a limited, if any of the device extends towards the buttocks of the wearer, thereby minimizing bunching and discomfort". Similarly the device disclosed in UK 1,092,274 is provided with a narrow aperture width towards the rear part of the user where a wedge is said to be snuggly fit into the groove between the labia in the lower area just above the rectum and below the vagina. Also the bag disclosed in this UK reference is formed such that it is apparently intended not to cause discomfort to the wearer, especially in the rearward portion of the article.

It has, however, now been found that the leakage and thereby soiling performance of devices or articles having an oblong shape with a wider front aperture and a narrower rear aperture, despite their indicated improvements and comfort, are dissatisfactory in respect to leakage performance and secure collection of menstrual fluids or vaginal discharges.

In addition to the aspects just mentioned, there is also a need to improve the application of collection container devices to the wearer such that their positioning is controlled and their attachment to the skin of the wearer is providing a secure seal against leakage.

Hence there is still a need to provide an article which can be effectively utilized to collect and absorb menstrual fluids and the like and thereby prevent leakage and soiling, whilst being comfortable to wear, having dimensions which allow the product to be worn discretely, and being applied in a controlled and secure sealing manner.

SUMMARY OF THE INVENTION

The present invention relates to a disposable menstrual fluid management device (10). The disposable menstrual fluid management device (10) comprises a bag (11), having an aperture (13) being surrounded by an adhesive (12) for releasable attachment to the uro-genital area of the wearer. An absorbent material (15) is contained within said bag. The aperture has an oblong shape and a front and a rear end. The aperture and the surrounding adhesive have a transverse dimension, which is wider in the rear half of the article than in the front half of the article. The adhesive is preferably protected by a release material having a longitudinal slit at its rear end together with a pull tab attached to the release liner for removal of the release liner during (not prior to) application, after a small portion of the adhesive has been exposed and attached already to the wearer.

BRIEF DESCRIPTION OF THE DRAWINGS

While the specification concludes with claims pointing out and distinctly claiming the present invention, it is believed the same will be better understood by the following drawings taken in conjunction with the accompanying speci

DETAILED DESCRIPTION OF THE INVENTION

The term "disposable" as used herein describes devices which generally are not intended to be laundered or otherwise restored or reused (i.e., they are intended to be discarded after a single use and, preferably, to be recycled, composed or otherwise disposed of in an environmentally compatible manner.

According to the present invention the term menstrual fluid as used herein, refers to all discharges produced during the menstruation period. Of course the devices according to the present invention can also collect female discharges produced outside of that period.

Figure 1:
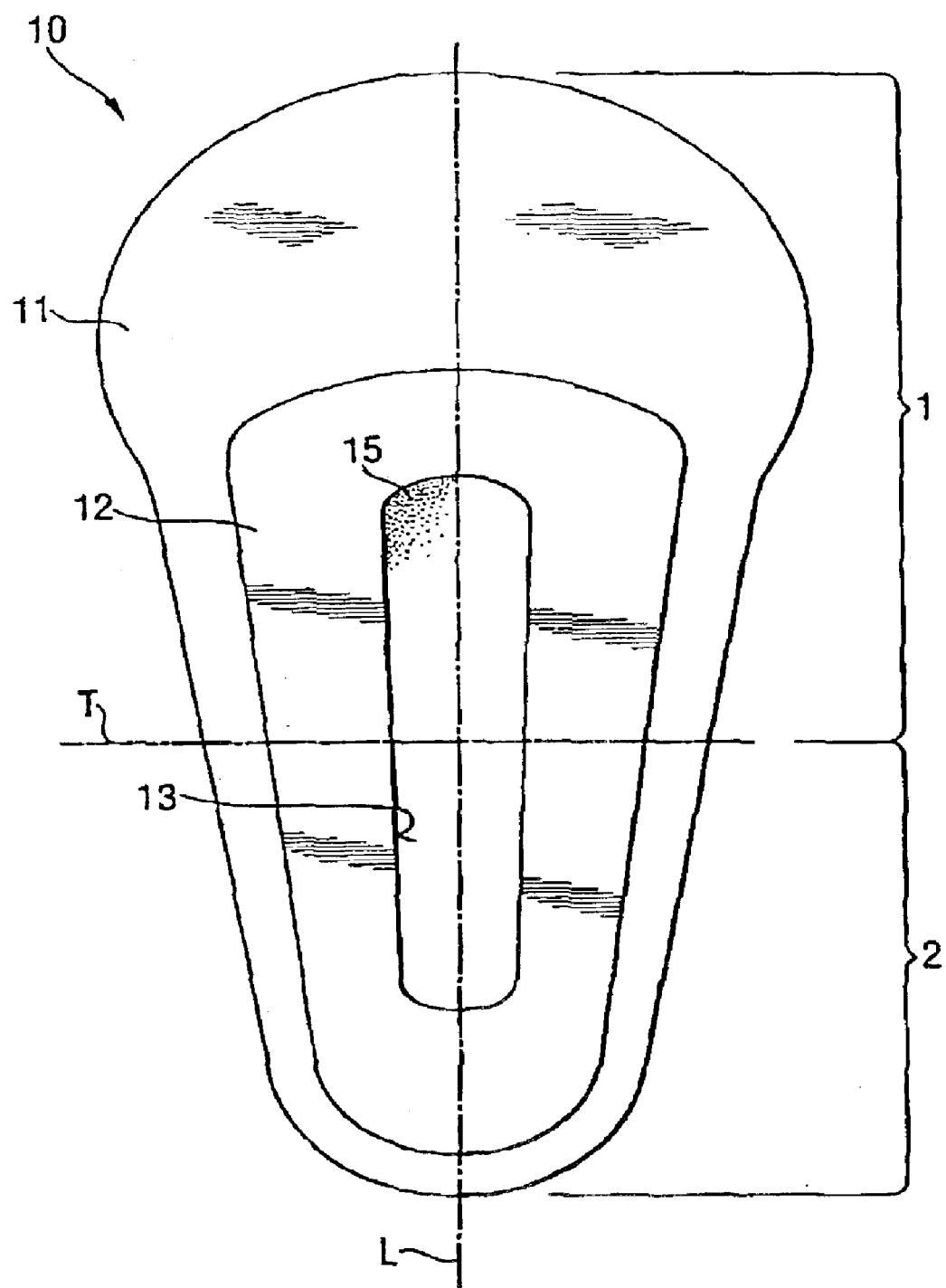
FIG. 1 is a plan view of a disposable menstrual fluid management device of the prior art.

Referring now to FIG. 1, there is shown a disposable menstrual fluid management device (10) according to the prior art U.S. Pat. No. 6,761,710 B2. For a detailed description of this prior art device it is referred to the European Patent publication dated Jun. 6, 2001. Since the present invention is directly based on this prior art, the disclosure of all aspects of this prior art fluid management device, especially as to the selection of materials, designs, manufacturing and processing indications are expressly referred to hereby and incorporated by reference.

In general disposable menstrual fluid management devices (10) comprise a bag (11) having an aperture (13) and an adhesive (12) surrounding the aperture for attachment to the body of a wearer. The device further has a longitudinal axis L and a transverse axis T, which is perpendicular to the longitudinal axis L and goes through the center of the aperture (13). The transverse axis also separates the article into a first and a second half (1 and 2). In the prior art device shown in FIG. 1, the first part is intended to be worn pointing towards the front or belly side of a female user of such a device, while the second part of the device (2) is intended to be worn pointing towards the back, or buttock of the wearer in such a way, that the longitudinal end of the article does not overlay the anus of the female user of such a device.

The difference of the device according to the present invention that is otherwise the same as the prior art device, according to U.S. Pat. No. 6,761,710 B2, is clearly shown in FIG. 2 in that the aperture (13) is wider in one part of the device while the same is true for the adhesive flange (12) and the article bag (11). Importantly the wider part of the aperture (13), and thereby of the device (10), is in the second part of the article which is intended during use of the device to be oriented towards the back of the female user, i.e. pointing towards the back. Importantly it has been found by the inventors of the present application that the female genital area is better suited when the aperture provides for the wider genital in the rear to be aligned with the aperture while the comfort of the device is not substantially compromised. This design does also provide for a substantially better sealing of the adhesive since at least in the rear portion it reaches skin regions with less pubic hair, thereby increasing the sealing performance of the adhesive and the prevention of leakage thereby.

Figure 2:
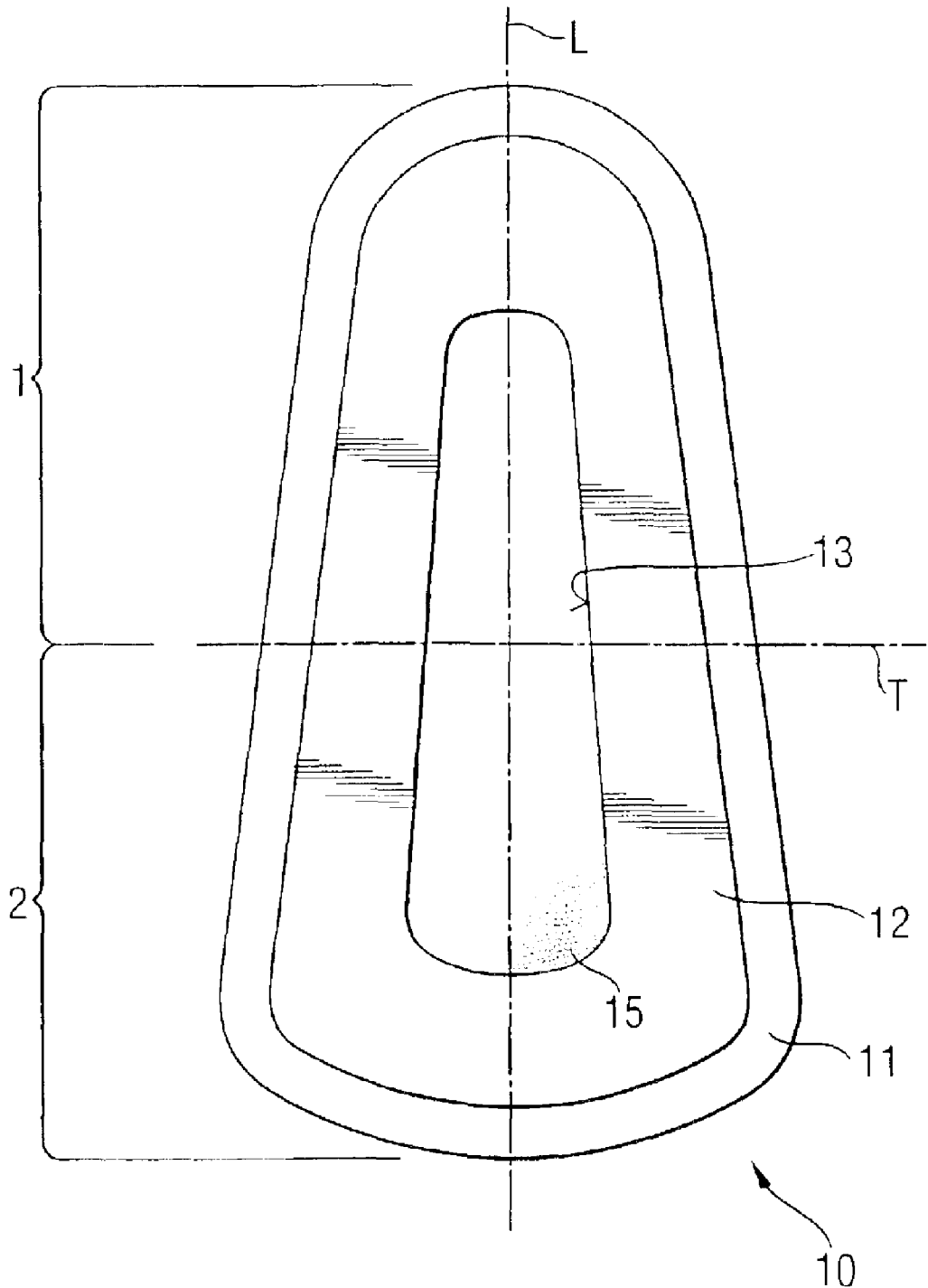
FIG. 2 is a plan view of the disposable menstrual fluid management device of the present invention.

As a preferred design, the shape shown in FIG. 2 can be considered. However, variations in the shape are possible and depending on various aspects may be desirable. In order to provide dimensional guidance as to the increase in width for the aperture between the front and the rear portions of the device, it can be said that the width dimension of the aperture measured in the center of the front portion of the device in relation to the width dimension measured in the center of the rearward portion of the device, should be on the order of less than 0.95, preferably less than 0.9, more preferably less than 0.8 and most preferably between 0.5 and 0.8.

Conventionally the flange, as also shown in the prior art, with its adhesive, will completely surround the aperture (13). In principle it is, however, also possible and maybe desirable depending on the targeted user group, that the flange, or at least the adhesive, is not completely surrounding the aperture. A "U" shape of the flange and/or the adhesive may be selected where the open part of the flange and/or the adhesive is directed towards the front of the wearer during use so as not to create difficulties in the context of the pubic hair primarily growing in the front of the genital area or the targeted user group. This open portion of the flange and/or the adhesive will hence be positioned in the first portion (1) of the device (10). Another modification may be that the flange outside or inside edge is not linear, but provided as a sinusidal wave edge which has been found to provide additional comfort, especially upon removal of the article.

It is also possible that the bag (11) of the device extends, preferable at the back end of the device, significantly beyond the region to which the flange (12) extends. This is in practice again no difference than the prior art device as shown in FIG. 1 where the bag (11) extends on the front end substantially beyond the flange periphery, except that the aperture at the front end of the prior art device was longer than in the present invention. Further it is also possible in preferred embodiments that the bag (11) material is fully or partially breathable (i.e. water vapour pervious) and made from materials such as non-woven material, monolythic film, microporous film, apertured film or laminates of such materials or mixtures of such materials. Of course the basic function of the bag to collect and store fluid has to be satisfied.

In order to put the preferred embodiment of the disposable fluid management device according to the present invention into practice, the adhesive on the flange requires protection prior to use of the device. The usual way of protecting an adhesive layer is to cover it with a release liner, preferable the release liner materials as disclosed in prior art ref. U.S. Pat. No. 6,761,710 B2 can be used. The most preferred release liner is a durable film material coated such that the release function is easily achieved while having sufficient tensile strength to allow shearing the release liner film away from the adhesive in practically any direction desirable. The release liners according to the present invention can of course also be used in conjunction with the prior art devices as for example shown in FIG. 1, however they are most effectively in combination with the device according to the present invention, since the design of the present invention due to the wider rear end improves placement accuracy and attachment of the article already.

Figure 3:
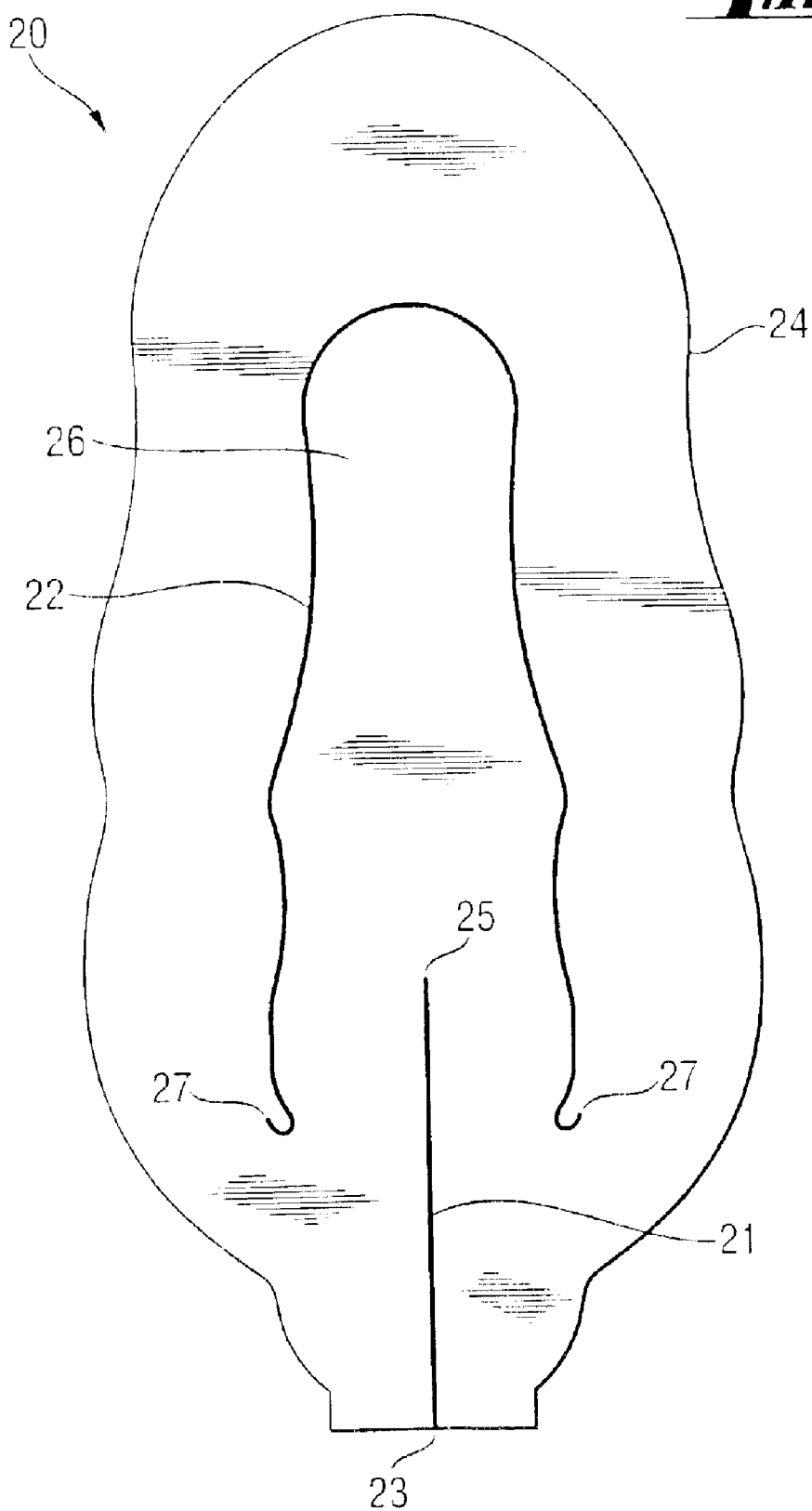
FIG. 3 is a plan view of a release liner according to the present invention.

As shown in FIG. 3, a release liner (20) is shown. The release liner has an outer peripheral design (24) that is at least as large, but could also be extending beyond the outer flange (12) dimension of the device (10). The release liner has two main surfaces, at least one of which needs to provide the release function for the adhesives used on the device (10) discussed above. The typical surface for this release function should be hydrophobic, or more generally having a low surface energy. Surfaces, such Teflon surfaces or silicon surfaces have proven to be very useful and coatings with such materials have been used in the art. The release liner has a slit (21). This slit is positioned such that when used in conjunction with the device (10) it is aligned and overlays the longitudinal centerline L in the rearward, or second portion of the device. The slit has a length from the peripheral point of the release liner (23) to the end of the slit (25) such that the end point (25) of the slit will reach a point in conjunction with the device (10), which is inside the aperture (13).

The peripheral point (23) on the release liner where the slit originates, should on the other hand preferably extend beyond the flange (12) of the device (10) when the release liner is placed on the adhesive of the device prior to use. This allows to grip the release liner at the peripheral region next to peripheral point (23) and peal the release liner off from the device (10) thereby exposing the adhesive from the flange and allowing the device to be bent downwards along the longitudinal centerline L of the device, thereby forming a wedge-shaped adhesively exposed region for application between the rearward portion of the labia majora and the anus of the female wearer of such devices. Once this region has been attached, the release liner provides for further removal by use of the tongue (26) formed by the slit (22) and pulling on this tongue in a direction away from peripheral point (23).

It should be noted that the slit (22) must be within the peripheral region of the aperture when the release liner (20) is on the adhesive of the device (10). Thereby the tongue (26) is not adhesively attached to the device and can easily be grasped by the application person of the device (10).

In a preferred embodiment, the endpoint (25) of the slit is further away from the peripheral point (23) than the end points (27) of the slit (22). This will facilitate a folding round of the release liner prior to original application to the wearer of such device (10) so that pulling the tongue (26) to shear off the release liner from the adhesive is easier facilitated.

Figure 4:
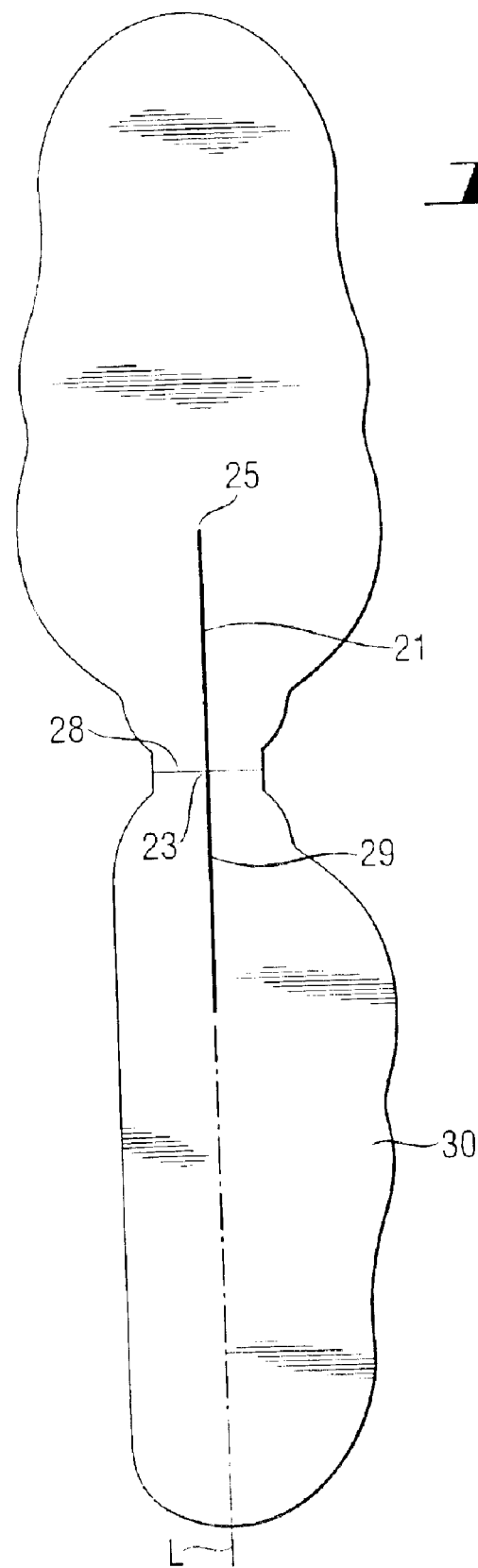
FIG. 4 is a plan view of an alternative embodiment of a release liner according to the present invention.

An alternative embodiment providing the same benefits as the release liner shown in FIG. 3 but simplifying the cutting process by eliminating the need for the tongue (26) cut (22) is shown in FIG. 4. In this Figure, the release liner, instead of having the tongue (26) formed by cut (22) is provided with a folding line (28) (this may e.g. be a sealing/welding line between two layers of release liner across which a mirror image of the release liner or any other shape of the release liner (both alternatives are shown by having a different peripheral edge on the right and left side of the drawing in the mirror image of the release liner shown in FIG. 4). The simplified version of the release liner as shown in FIG. 4 does require some additional material while at the same time eliminating the need for the complex cutting in a non-linear fashion shown in FIG. 3. It should be noted that the slit (21) needs to have a mirror image slit (29) in the mirror image portion of the release liner.

The mirror image portion (30) of the release liner needs not necessarily be capable of providing a release liner function. Again, when applying the device (10) to the body of a wearer, the application person (wearer or caretaker) takes the device, folds it downwards along the longitudinal center line so as to form a wedge for application to the wearer, peals off the release liner on both sides of the longitudinal center line of the wedge which is facilitated by slit (21) and can apply the exposed wedge shaped adhesive flange portion formed to the respectively wedge shaped region between the labia majora and the anus of the user of device according to the present invention. Then the function provided by the tongue (26) of the release liner in FIG. 3 is provided by the mirror image portion (30) of the release liner shown in FIG. 4. By pulling the release liner off the remainder of the flange (12) of the device (10) the application person just has to gradually attach the adhesive to the skin of the wearer of a device according to the present invention.

While particular embodiments of the present invention have been illustrated and described, it would be obvious to those skilled in the art that various other changes and modifications can be made without departing from the invention. It is therefore intended to cover in the appended claims all such changes and modifications that are within the scope of this invention.

What is claimed is:

1. A disposable menstrual fluid management device comprising a bag, said bag having an aperture, said aperture being surrounded by an adhesive for releasable attachment to the uro-genital area of a wearer, said device having a longitudinal axis L and a transverse axis T, said axis T being perpendicular to said axis L and going through the center of said aperture, said axis T dividing said device into a first portion and a second portion, said second portion being positioned during use of said article towards the back of a wearer and the width of said aperture is wider in said second portion of said device than in said first portion of said device and wherein said adhesive has an outer periphery having the same shape as said aperture.

2. The disposable menstrual fluid management device of claim 1 wherein the ratio of the width as defined herein in said first portion to the width in said second portion is less than 0.95.

3. The disposable menstrual fluid management device of claim 2 wherein said ratio is less than 0.8.

4. The disposable menstrual fluid management device of claim 3 wherein said ratio is between 0.5 and 0.8.

5. The disposable menstrual management device of claim 1 wherein said adhesive is protected prior to use by a release liner.

6. The disposable menstrual fluid management device of claim 5 wherein said release liner has a slit aligned with said longitudinal center line L, said slit extends from a peripheral point of said release liner to a point of said release liner which overlays said aperture.

7. The disposable menstrual fluid management device of claim 1 wherein said bag comprises an absorbent material selected from the group consisting of comminuted wood pulp; creped cellulose wadding; meltblown polymers; chemically stiffened, modified or cross-linked cellulosic fibers; tissue; absorbent foams; absorbent sponges; super-absorbent polymers; absorbent gelling materials, and mixtures thereof.

8. The disposable menstrual fluid management device of claim 7 wherein the material of said bag is breathable.

9. The disposable menstrual fluid management device of claim 7 wherein said bag further contains an odour control material.

10. The disposable menstrual fluid management device of claim 1, wherein said adhesive is a hydrogel adhesive.

* * * * *